United States Patent
Elen et al.

(10) Patent No.: US 9,983,143 B2
(45) Date of Patent: May 29, 2018

(54) METHOD AND APPARATUS FOR RAPIDLY COOLING A GEM

(75) Inventors: Shane Elen, Snohomish, WA (US);
Matt Hall, West Chester, PA (US);
Wuyi Wang, Edison, NJ (US)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 1075 days.

(21) Appl. No.: 12/380,416

(22) Filed: Feb. 27, 2009

(65) Prior Publication Data
US 2010/0218928 A1 Sep. 2, 2010

(51) Int. Cl.
*F28F 7/00* (2006.01)
*G01N 21/87* (2006.01)
*B01L 7/00* (2006.01)

(52) U.S. Cl.
CPC .............. *G01N 21/87* (2013.01); *B01L 7/50* (2013.01); *B01L 2300/1894* (2013.01)

(58) Field of Classification Search
CPC ...... F28F 7/00; B01L 7/50; B01L 2300/1894; G01N 21/87
USPC .......................... 165/185, 80.5, 132; 356/30; 250/341.1–341.2
See application file for complete search history.

(56) References Cited

U.S. PATENT DOCUMENTS

| | | | |
|---|---|---|---|
| 3,176,472 A * | 4/1965 | Cox ................................ 62/3.6 |
| 4,506,547 A * | 3/1985 | Kunze ...................... G01N 3/18 73/150 R |
| 4,578,963 A * | 4/1986 | Sitte ......................... G01N 1/42 62/383 |
| 4,955,204 A * | 9/1990 | Pehl et al. ...................... 62/51.1 |
| 5,118,181 A * | 6/1992 | Yifrach et al. ................... 356/30 |
| 5,644,919 A * | 7/1997 | Baker et al. .................... 62/45.1 |
| 5,876,118 A * | 3/1999 | Vogel .................. G01N 25/4826 374/11 |
| 6,377,340 B1 * | 4/2002 | Anthony ........... G02F 1/134327 349/110 |
| 7,130,037 B1 * | 10/2006 | Lange ................. G01N 21/9501 356/237.2 |
| 7,324,188 B1 * | 1/2008 | Beesley ........................... 356/30 |
| 2008/0092556 A1 * | 4/2008 | Stein et al. ..................... 62/45.1 |
| 2009/0019865 A1 * | 1/2009 | Henderson et al. .............. 62/62 |

* cited by examiner

Primary Examiner — Travis Ruby
(74) Attorney, Agent, or Firm — DLA Piper LLP (US); Gerald T. Sekimura

(57) ABSTRACT

A cooling apparatus includes a container configured to contain a coolant within a space. The apparatus further includes a cooling block positioned substantially within the space and having a high heat capacity such that the space not occupied by the cooling block is filled with a coolant to a level at or below the top of the cooling block, and a placement structure having high thermal conductivity positioned on top of the cooling block and outside of the space. A method for cooling an object is also provided, which includes inserting a coolant into a container configured to contain the coolant within a space, and placing the object on a placement structure outside the space. For this method, the placement structure has a high thermal conductivity and is coupled to a cooling block, the cooling block having a high heat capacity and positioned substantially within the space.

22 Claims, 10 Drawing Sheets

METHOD AND APPARATUS FOR RAPIDLY COOLING A GEM

TECHNICAL FIELD

The present invention is directed generally towards cooling an object, and more specifically towards a method and apparatus for rapidly cooling a gem so as to facilitate spectral analysis.

BACKGROUND OF THE TECHNOLOGY

It is often desirable to analyze properties of an object that has been cooled to very low temperatures, such as cryogenic temperatures, for example temperatures close to that of liquid nitrogen. When analyzing a gem, for example, it is often desirable to perform a spectral analysis of the gem at cryogenic temperatures to obtain information about the composition of the gem. Performing a spectral analysis on a gem cooled to such temperatures is particularly useful, for example, in determining the color origin of diamonds which may have been subjected to various treatments such as irradiation, as in a nuclear reactor or by an electron beam, or annealing, and for identifying diamonds treated under high-pressure and high-temperature (HPHT).

Currently available cooling apparatuses exhibit a number of disadvantages. For example, some currently available cooling apparatuses require a test sample to be cooled for approximately 20-30 minutes before a spectral analysis could be performed. Such a prolonged cooling period severely limits production capacity when a large number of gems need to be analyzed. Other apparatus employ direct immersion of the gemstone in the cooling medium which may result in undesirable interaction between the cooling medium and spectral information of interest. Still other cooling arrangements have employed a cylindrical copper block of approximately 2 inches in diameter, 1.8 inches in height, and having a 0.16 inch diameter bore along its axis, and which has been cooled to a desired temperature and removed from the cooling environment prior to placement of the object to be cooled in the 0.16 inch diameter bore.

Another disadvantage of some of the currently available cooling apparatuses is that they are bulky and complex. Some of these apparatuses, for example, require the test sample to be placed within a shell that is submerged in liquid nitrogen. Because of condensation that may occur within the shell, however, such apparatuses require a mechanism to infuse moisture-free gas into the enclosed internal chamber occupied by the test sample. As such, in addition to the extra time required to infuse gas into the shell, these apparatuses add additional costs to the analysis task, and because of their complexity are more prone to mechanical failure.

Accordingly, there is a need for a method and apparatus for rapidly cooling gems in an efficient and cost effective manner. More specifically, there is a need for a method and apparatus for cooling gems which does not require a closed environment, or infusion of moisture-free gas, and which allows for a rapid cool down and analysis of a large number of gems.

SUMMARY OF THE INVENTION

The present invention addresses the aforementioned problems by providing an improved method and apparatus for rapidly cooling gems in connection with analyzing the gems. An embodiment of the present invention provides a cooling apparatus which includes a container having walls, such that the container is configured to contain a coolant within a space enclosed by the walls. The apparatus further includes a cooling block positioned substantially within the space and having a high heat capacity. The portion of the space not occupied by the cooling block is filled with a coolant to a level at or below the top of the cooling block. Such an embodiment also includes a placement structure having a high thermal conductivity positioned on top of the cooling block and outside of the coolant-filled space.

In another embodiment a cooling apparatus is provided including a container having an open end and a cooling block positioned within the container. For this embodiment, the cooling block has a high heat capacity, and a space between the cooling block and walls of the cooling apparatus is filled with a coolant to a level at or below the top of the cooling block. A placement structure having a high thermal conductivity is also provided, which is positioned outside of the coolant-filled space and in contact with a face of the cooling block that is accessible at the open end of the container.

In another embodiment of the present invention, a method for cooling an object is also provided, which includes inserting a coolant into a container configured to contain the coolant within a space and placing the object on a placement structure outside the space. Within such embodiment, the placement structure has a high thermal conductivity and is coupled to a cooling block. Also within this embodiment, the cooling block has a high heat capacity and is positioned substantially within the space.

In a further embodiment, a cooling apparatus is provided which includes a container configured to contain a coolant within a space. Within such embodiment, a cooling block having a high heat capacity is positioned substantially within the space such that the space not occupied by the cooling block is filled with a coolant to a level at or below the top of the cooling block. The apparatus also includes a placement structure having a high thermal conductivity, such that the placement structure is coupled to the cooling block and isolated from the space.

In another embodiment of the present invention, a method for cooling an object is provided, which includes pouring a coolant into a space bounded by a container and positioning the object on a placement structure having a high thermal conductivity. Within such embodiment, the placement structure is coupled to a cooling block having a high heat capacity and positioned substantially within the space, such that the object is isolated from the space.

Through the use of a device and method in accordance with the present invention spectral patterns have been obtained which much more accurately reflect the color of analyzed samples.

As will be appreciated upon consideration of the following detailed description of the invention and accompanying drawings, there are many advantages and features of the present invention, which in turn lead to many new and useful applications of the invention.

DETAILED DESCRIPTION OF THE INVENTION

The present invention is directed towards providing an improved method and apparatus for cooling objects by the use of a coolant. In a particular application, the present invention provides an efficient open to the air solution for rapid cooling of gems to cryogenic temperatures, for use in a system that perform spectral analysis of gems at such temperatures. Moreover, for such applications, a significant improvement from prior art methods and apparatuses is provided since the present invention cools gems much faster and does not require complex mechanisms that infuse moisture-free gas. Such an improvement is particularly useful when a large number of gems need to be individually analyzed.

Figure 1:
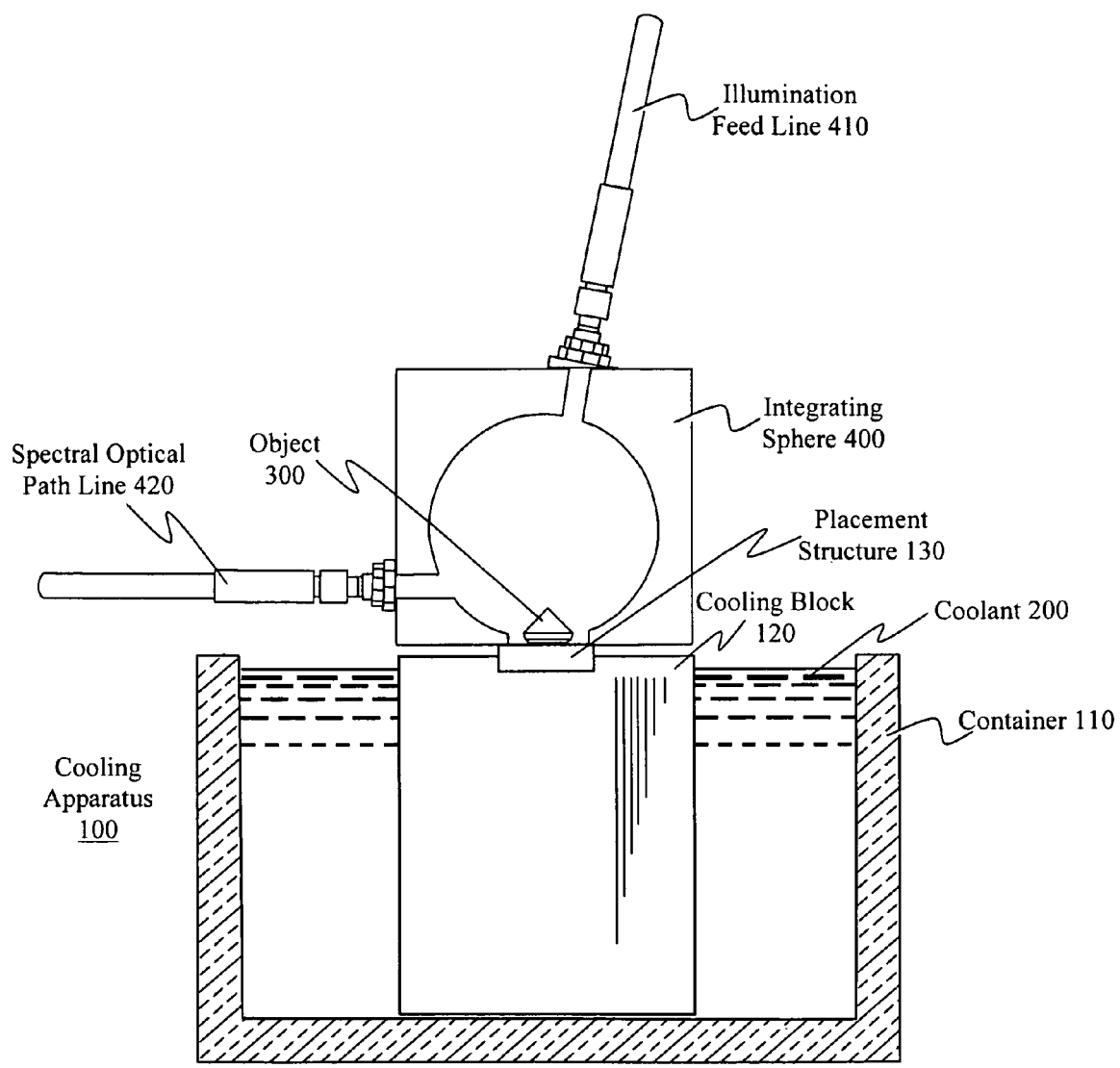
FIG. 1 is an exemplary cooling apparatus having low walls according to an embodiment of the invention.

In FIG. 1, an exemplary cooling apparatus according to an embodiment of the invention is provided. As illustrated, a cooling apparatus 100 includes a container 110, a cooling block 120, and a placement structure 130. In a preferred embodiment, placement structure 130 is positioned on top of cooling block 120, and cooling block 120 is positioned in the center of container 110, as shown.

In use, cooling apparatus 100 may be used in conjunction with an integrating sphere 400 to analyze the spectral properties of an object 300 cooled to a desired temperature. Within such embodiment, the space between cooling block 120 and container 110 is preferably filled with a coolant 200 (e.g., liquid nitrogen) to a height just below the top of cooling block 120, as shown. By selecting a cooling block 120 with a sufficiently high heat capacity, and by selecting a placement structure 130 with a sufficiently high thermal conductivity, object 300 is quickly and effectively cooled to the desired temperature. Preferably, the sample is first cooled down to the coolant (e.g. liquid nitrogen) temperature quickly by direct immersion in coolant, then transferred to the block. In this way, the sample is cooled down even faster, and also properly maintained. Once object 300 is cooled, integrating sphere 400 may then be positioned over object 300 and about placement structure 130 as shown. Object 300 may then be illuminated via illumination feed line 410, and spectral response information may then be collected via spectral optical path line 420.

In the discussion that follows, the structural dimensions of various aspects of the present invention are discussed, and dimensions for a particular embodiment are given. However, it should be noted that such dimensions are provided solely as an example of particular embodiments and are not intended to limit the scope and spirit of the invention. Furthermore, it will be apparent to one skilled in the art upon reading these descriptions that other materials, dimensions, configurations and arrangements can be used to implement the teachings of this application and the concepts of the present invention.

As shown in FIG. 1, the illustrated embodiment includes an insulation container 110 preferably having a rectangular cross section. A variety of container shapes may be used, including cylindrical and cubic shaped containers. In a prototype of cooling apparatus 100, insulation container 110 was made of Styrofoam® material, in which the walls had a height of approximately 20 cm uniform thickness of approximately 5 mm and the dimensions of the base were approximately 20 cm. For the particular embodiment of FIG. 1, it should be appreciated that the side walls were configured to have a uniform height substantially even with the height of cooling block 120, as shown.

Meanwhile, cooling block 120 fits substantially within insulation container 110, as shown, where it firmly rests either due to its weight alone or from being affixed to the base of insulation container 110. In a preferred embodiment, cooling block 120 has a cylindrical shape and has a high heat capacity, which provides a "heat sink" so that object 300 is cooled to a temperature at or about the temperature of cooling block 120. Cooling block 120 is preferably made from a material and has a mass such that the heat energy required to increase the temperature of cooling block 120 by a certain temperature interval is large, so that the object 300 being evaluated quickly reaches a temperature at or near the temperature of cooling block 120. In a preferred use of the embodiments of the cooling apparatus, a sample is first pre-cooled in coolant located either external to or within the container 110, and then placed upon the cooling block 120, which permits a very low temperature to be maintained by the block. Materials which have high heat capacity suitable for use in the invention include, for example, copper, iron, indium. In a prototype, cooling block 120 was made of copper having a height of approximately 70 mm and a diameter of approximately 63.5 mm.

Figure 2A:
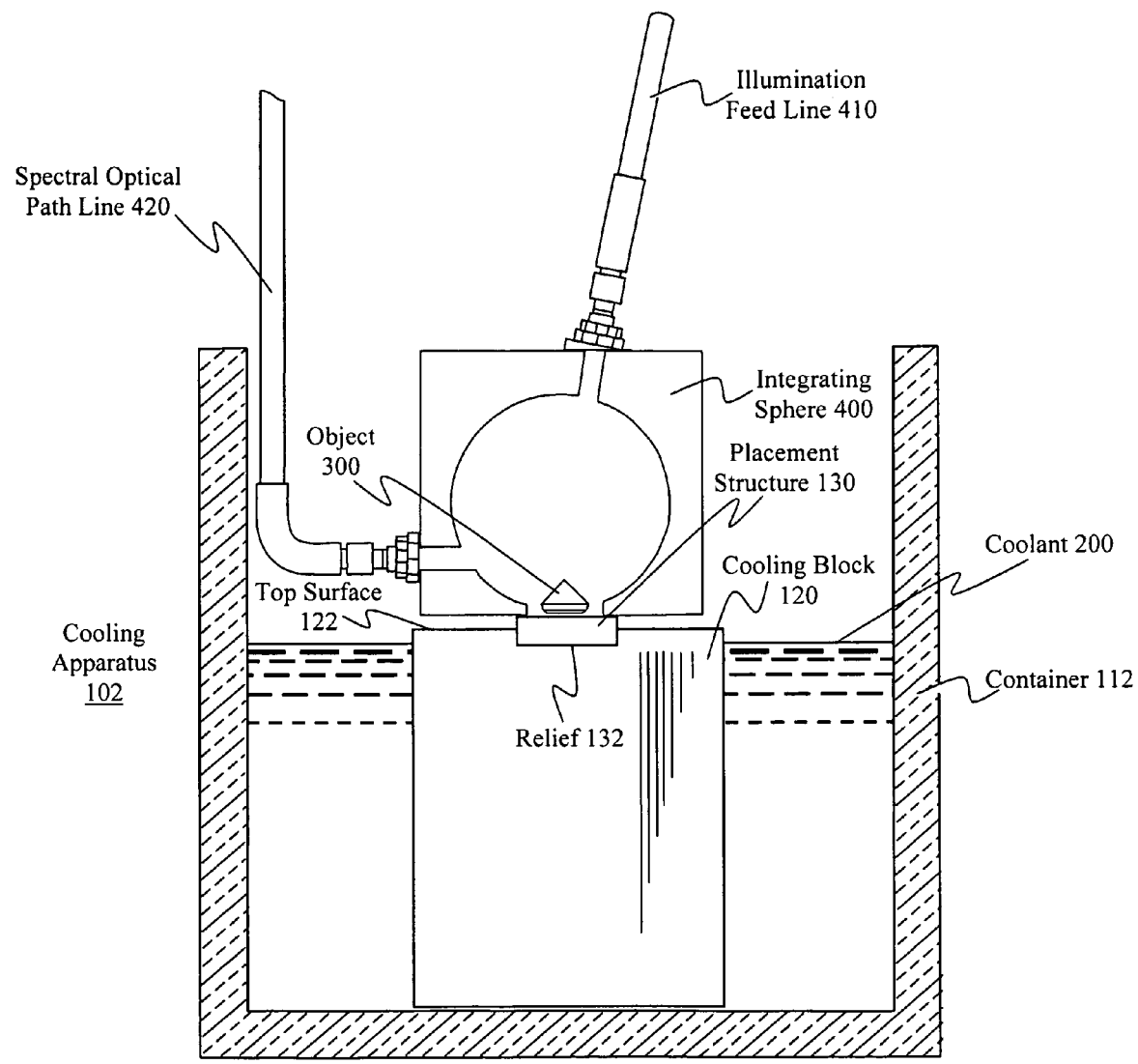
FIG. 2A is an exemplary cooling apparatus having high walls, wherein the spectral analysis optical path line is routed to enter the enclosed space through the open end of the container, according to an embodiment of the invention.
Figure 2B:
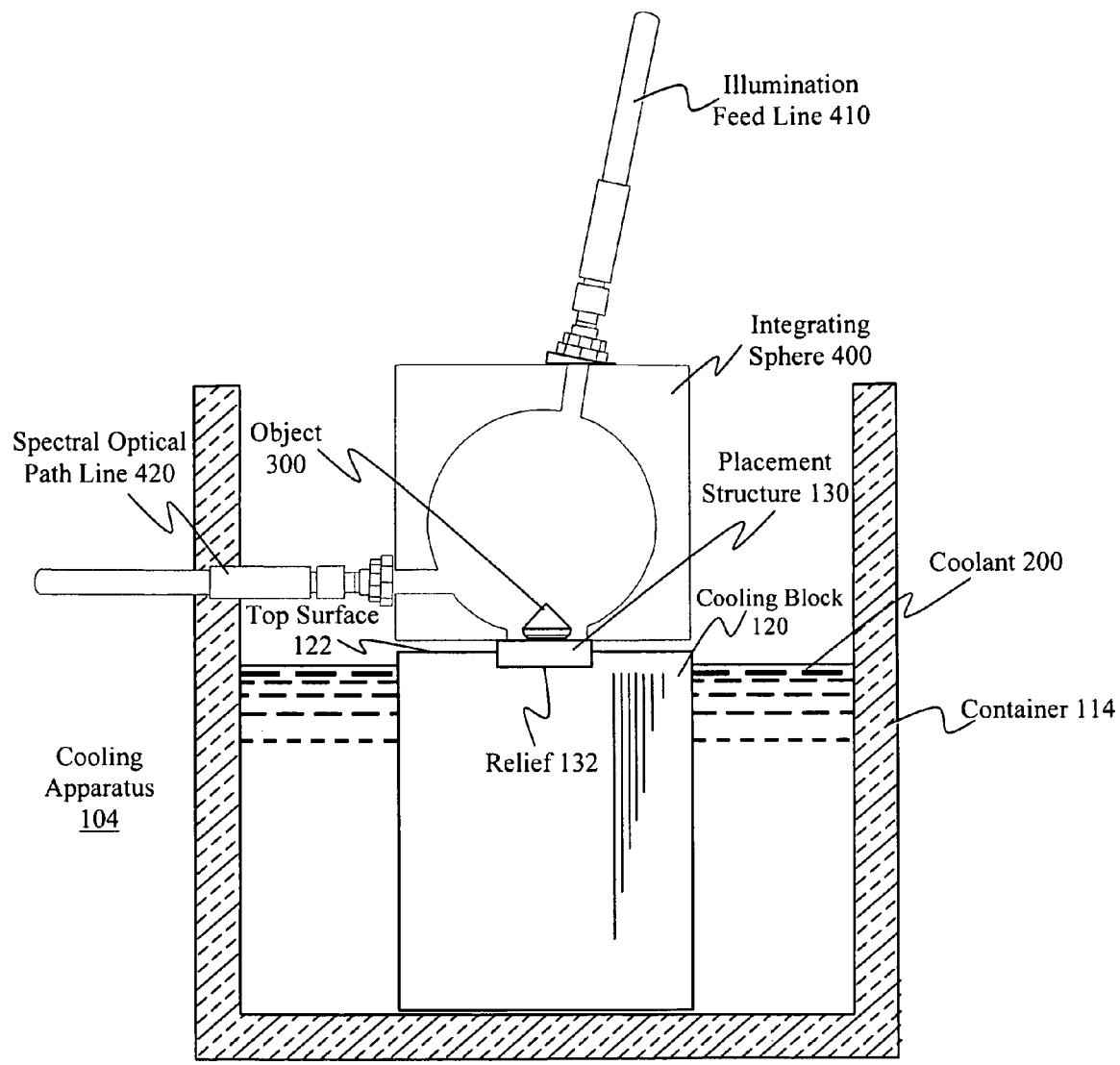
FIG. 2B is an exemplary cooling apparatus having high walls, wherein the spectral analysis optical path line is routed through a very narrow slit in the high walls that is dimensioned to accommodate an optical fiber, according to another embodiment of the invention.

Placement structure 130 is preferably positioned on top surface 122 of cooling block 120, as shown for example in FIGS. 2A and 2B, where it is preferably positioned within a relief 132 formed within the top surface 122. Placement structure 130 may be friction-fit into relief 132, affixed to top surface 122 by way of a suitable thermally conductive adhesive, or attached to top surface 122 through other suitable mechanisms which promote thermal conduction between placement structure 130 and cooling block 120. In a preferred embodiment, placement structure 130 is disc-shaped and has a high thermal conductivity so as to facilitate an efficient transfer of energy from object 300 to cooling block 120. Preferably, materials having thermal conductivity at or above that of high purity alumina or SPECTRALON® polymer material may be used for placement structure 130.

For some embodiments, the desired conductivity may be achieved by constructing placement structure 130 out of aluminum. For particular applications, however, it should be appreciated that placement structure 130 may need to exhibit properties not necessarily provided by aluminum. For spectral analysis, for example, a placement structure 130 that provides a background for object 300 that minimizes false readings, may be used. Also, the placement structure may be configured to promote coupling to integrating sphere 400. For such embodiments, placement structure 130 preferably utilizes materials with high thermal conductivity and which provide a "white" background, such as any of a plurality of materials including TEFLON®, white ceramic, boron silicate, and aluminum oxide. Placement structure 130 may be made entirely of such materials or such materials may be used to line the surface of placement structure 130. Placement structure 130 may thus be designed to provide both high thermal conductivity and a background having a desired absorption characteristics. In a preferred embodiment, placement structure 130 may be a disc of TEFLON® polymer material having a thickness of approximately 0.1 inch and a diameter of approximately 1.0 inch.

In a preferred embodiment, it should be appreciated that cooling apparatus 100 may be used for spectral analysis in conjunction with any of a plurality of commercially available integrating spheres 400. In a prototype, an integrating sphere 400 manufactured by Avantes BV, of Eerbeek, Netherlands, was used, which included an illumination feed line 410 and a spectral optical path line 420, as shown. During use, integrating sphere 400 is coupled to placement structure 130 so as to substantially cover object 300. Illumination feed line 410 provides light to the inner portion of integrating sphere 400 so as to provide illumination for object 300. Spectral optical path line 420 provides an optical path for communicating the resulting spectral response of object 300 to analysis equipment such as a spectrometer. The above arrangement facilitates spectral analysis of object 300 which has been cooled by cooling apparatus 100.

In a preferred embodiment of the invention, as illustrated in FIGS. 2A and 2B, the walls of container 112 (and container 114) are designed to extend to a height substantially higher than the height of cooling block 120, and thereby to extend to a height substantially higher than the top of object 300 when placed on placement structure 130, as shown. In a prototype, the walls were designed to extend approximately 2 inches higher than the height of object 300. By implementing such a design, when coolant 200 is in liquid form, such as dry liquid nitrogen, vaporized gas emanating from coolant 200 will fill the space above coolant 200 and displace the ambient gases from around object 300. The vaporized gas from coolant 200 may flow over the heightened walls of containers 112 or 114, for example, thus filling the interior space above cooling block 120 and coolant 200 with the vaporized gas. As a result, the vaporized gas is present above the top of cooling block 120 and serves as a dry atmosphere to prevent condensation on object 300.

When such an embodiment is used in conjunction with integrating sphere 400, it should be further noted that spectral optical path line 420 may either be routed along the interior and over the top of the walls of container 112, as shown in FIG. 2A, or through a wall of container 114, as shown in FIG. 2B. Preferably, for the configuration of FIG. 2B, a narrow slit, of about 5 mm in width, is provided for passage of the fiber through the container wall.

Figure 3A:
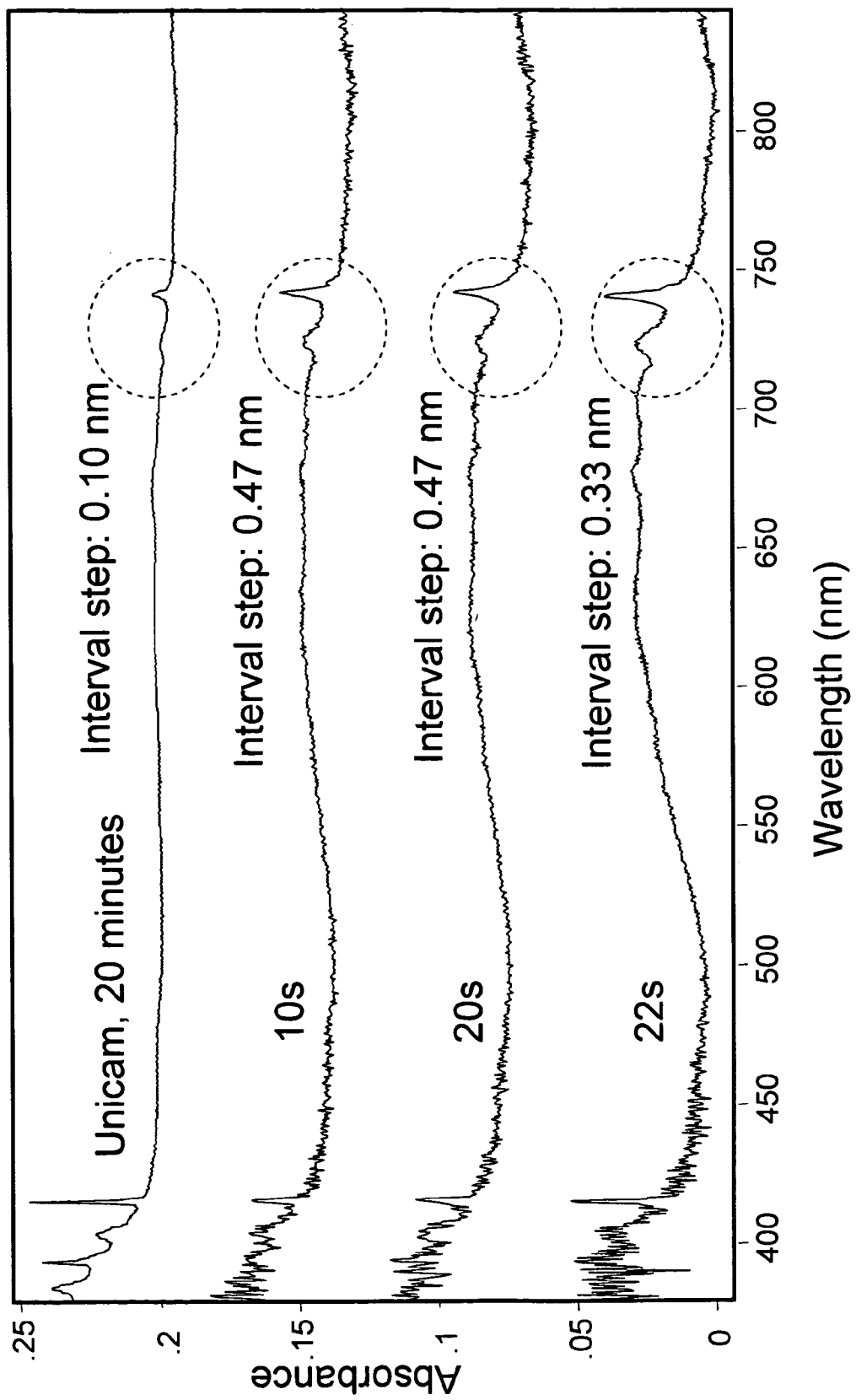
FIG. 3A is an exemplary graph comparing the spectral analysis of a 0.16 carat gem obtained using an apparatus of the prior art versus an apparatus according to an embodiment of the invention.
Figure 3B:
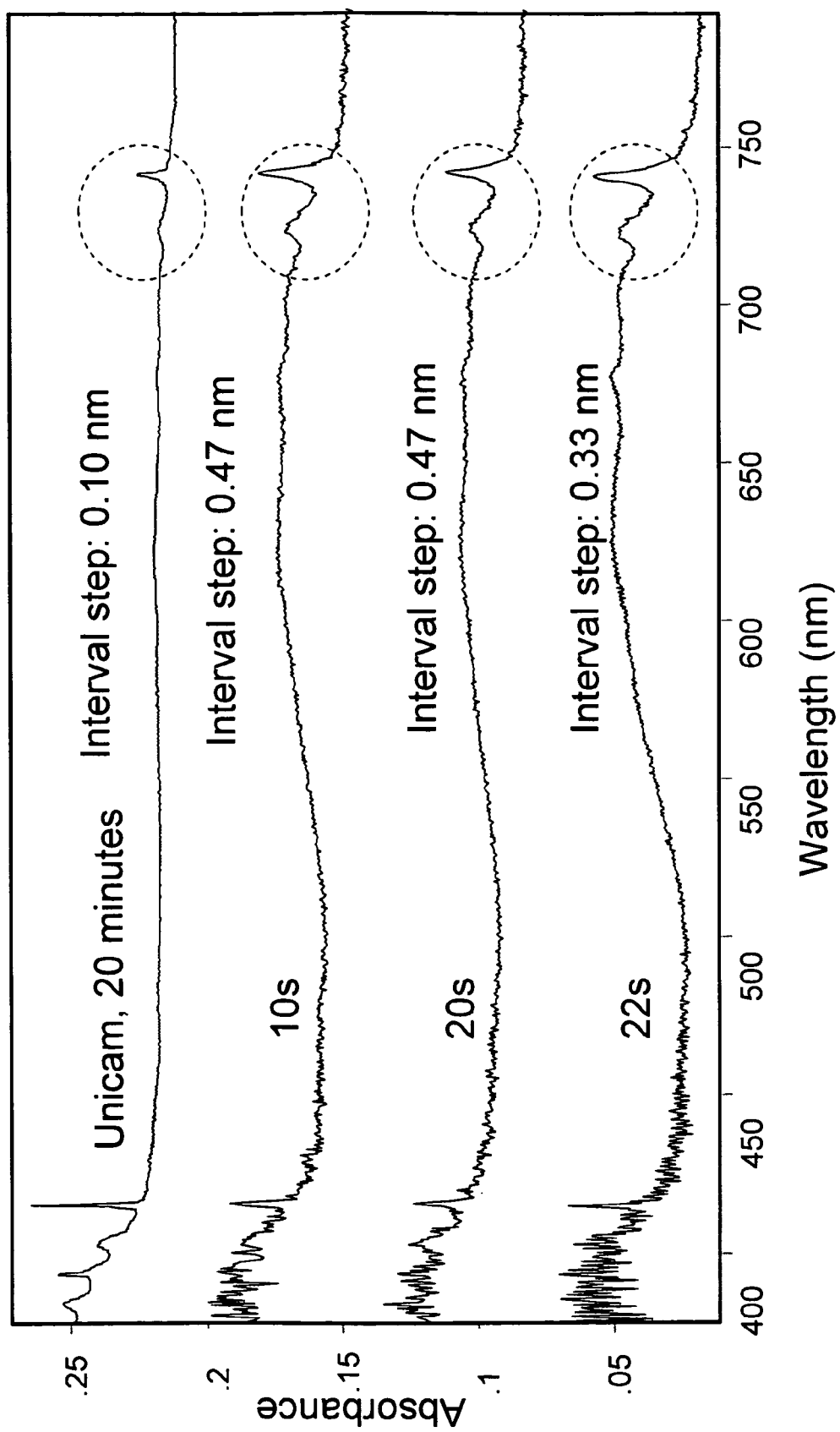
FIG. 3B is an exemplary graph comparing the spectral analysis of a 0.11 carat gem obtained using an apparatus of the prior art versus an apparatus according to an embodiment of the invention.
Figure 3C:
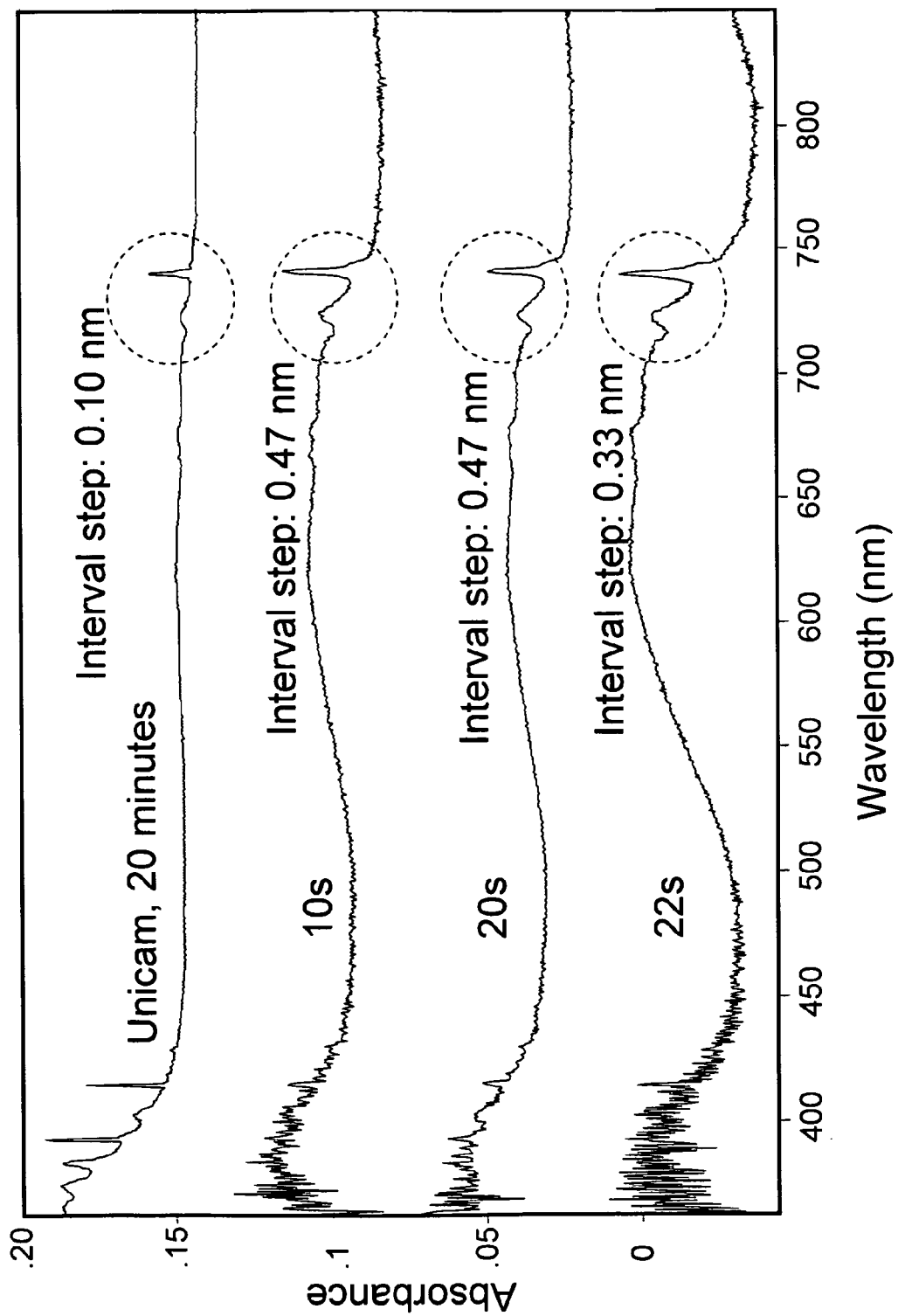
FIG. 3C is an exemplary graph comparing the spectral analysis of a 0.14 carat gem obtained using an apparatus of the prior art versus an apparatus according to an embodiment of the invention.

The present invention has provided a useful tool for performing spectral analysis on gems, which require the gems to be cooled to a particular temperature. Namely, relative to prior art apparatuses, the present invention provides a cooling apparatus which cools gems much faster and yields spectrums of much higher quality. To better illustrate the utility of the present invention, FIGS. 3A-3C provide charts illustrating a comparison of plots of spectral responses of gems weighing 0.16, 0.11, and 0.14 carats obtained using an apparatus of the prior art versus an apparatus according to an embodiment of the invention. In each of these charts, four plots are provided. One plot shows the spectrum obtained, plotted at an interval step of 0.10 nanometers, using a prior art apparatus in which the gem had been cooled for approximately twenty minutes. Using the prior apparatus, it takes about 20 minutes to get the sample cooled down and about another 20 minutes to collect a spectrum. The prior art apparatus employed a Unicam spectrometer with cryostat, provided by Thermo Elemental, of Franklin, Mass. The other three plots were obtained using embodiments of the present invention for spectral accumulation of the gem at each of ten, twenty, and twenty-two seconds, and plotted at interval steps of 0.47, 0.47, and 0.33 nanometers, respectively. A system by which the spectral information was analyzed and plotted to yield these plots is described in further detail in co-pending U.S. application Ser. No. 12/380,425, now issued U.S. Pat. No. 8,120,758, entitled "FAST UV-VIS-NIR ABSORPTION SPECTROMETER SYSTEM AND METHOD", filed even-date herewith, and incorporated by reference herein in its entirety. As illustrated, in addition to cooling the gems much more quickly than the prior art apparatus, the present invention provides a relatively higher quality spectrum that includes less noise for a wavelength region between 450 and 850 nanometers. In FIGS. 3A-3C, for example, the plotted response in the wavelength region between 700 and 750 nanometers has been circled to highlight the higher quality of the spectrums obtained, over a substantially shorter amount of time, using the present invention compared to that obtained though the prior art arrangement.

Figure 3D:
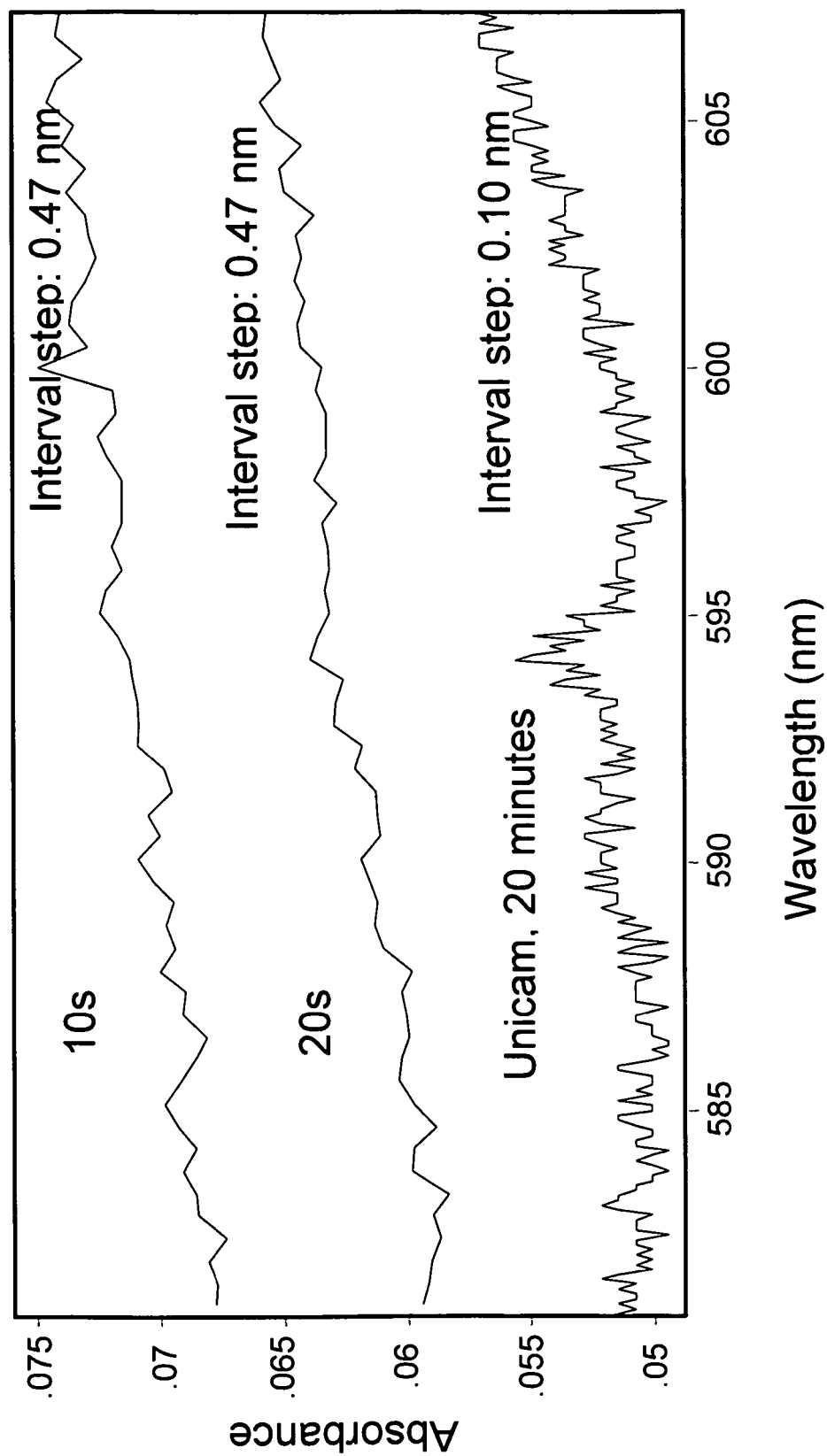
FIG. 3D is an exemplary graph comparing an enlargement of a portion of the spectral analysis of a 0.10 carat gem of FIG. 3C obtained using an apparatus of the prior art versus an apparatus according to an embodiment of the invention.

In FIG. 3D, an exemplary graph comparing the spectral response, over a 580 nm to 610 nm range, of a 0.10 carat gem obtained using an apparatus of the prior art versus an apparatus according to an embodiment of the invention is provided. For this particular graph, spectrum responses plotted at interval steps of 0.47 nanometers of the gem cooled by the present invention for each with spectral accumulation time of ten and twenty seconds are compared to a spectrum taken at an interval step of 0.10 nanometers of the same gem cooled by a prior art apparatus, which required a cooling time of approximately twenty minutes and another twenty minutes for spectral acquisition. As illustrated, FIG. 3D shows how quickly the spectrum obtained using the present invention "sharpens up" relative to the spectrum obtained by the prior art apparatus. FIG. 3D thus illustrates how rapidly spectral information can be obtained with reduced noise characteristics.

Figure 3E:
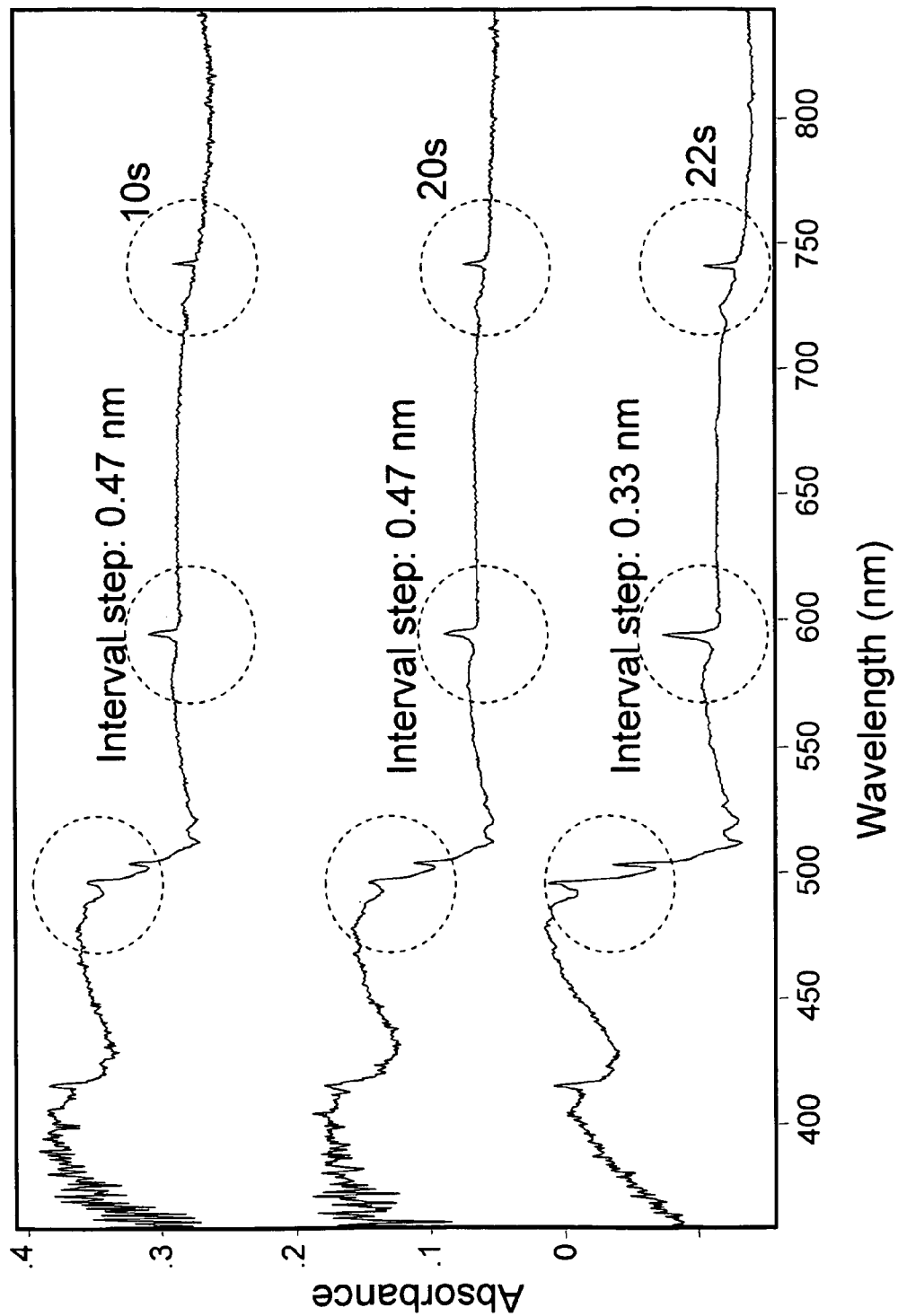
FIG. 3E is an exemplary graph comparing the spectral analysis of a 0.50 carat gem obtained at different cooling times using an apparatus according to an embodiment of the invention.

In FIG. 3E, an exemplary graph comparing the spectral analysis of a 0.50 carat gem obtained at different spectral accumulation times using an apparatus according to an embodiment of the invention is provided. In particular, three plots are provided which represent the spectra produced with accumulation time of ten, twenty, and twenty-two seconds, and at interval steps of 0.47, 0.47, and 0.33 nanometers, respectively. As illustrated, the spectrum produced with accumulation time of twenty-two seconds shows a relatively higher quality spectrum in terms of reduced noise than the spectrums produced with accumulation time of ten and twenty seconds. However, it is also to be noted that even after only 10 seconds of data accumulation, the spectrum peaks and general spectral characteristics are already apparent. In the wavelength region between 350-400 nanometers, for example, the plot representing the twenty-two second of data accumulation period exhibits much less noise than the plots representing the ten and twenty second accumulation periods. As illustrated, the peaks, while present in all of the plots, are also relatively more defined in the plot for the twenty-two second accumulation period compared to the plots for the ten and twenty second accumulation periods (see e.g., the peaks at approximately 503, 595, and 741 nanometers).

Figure 3F:
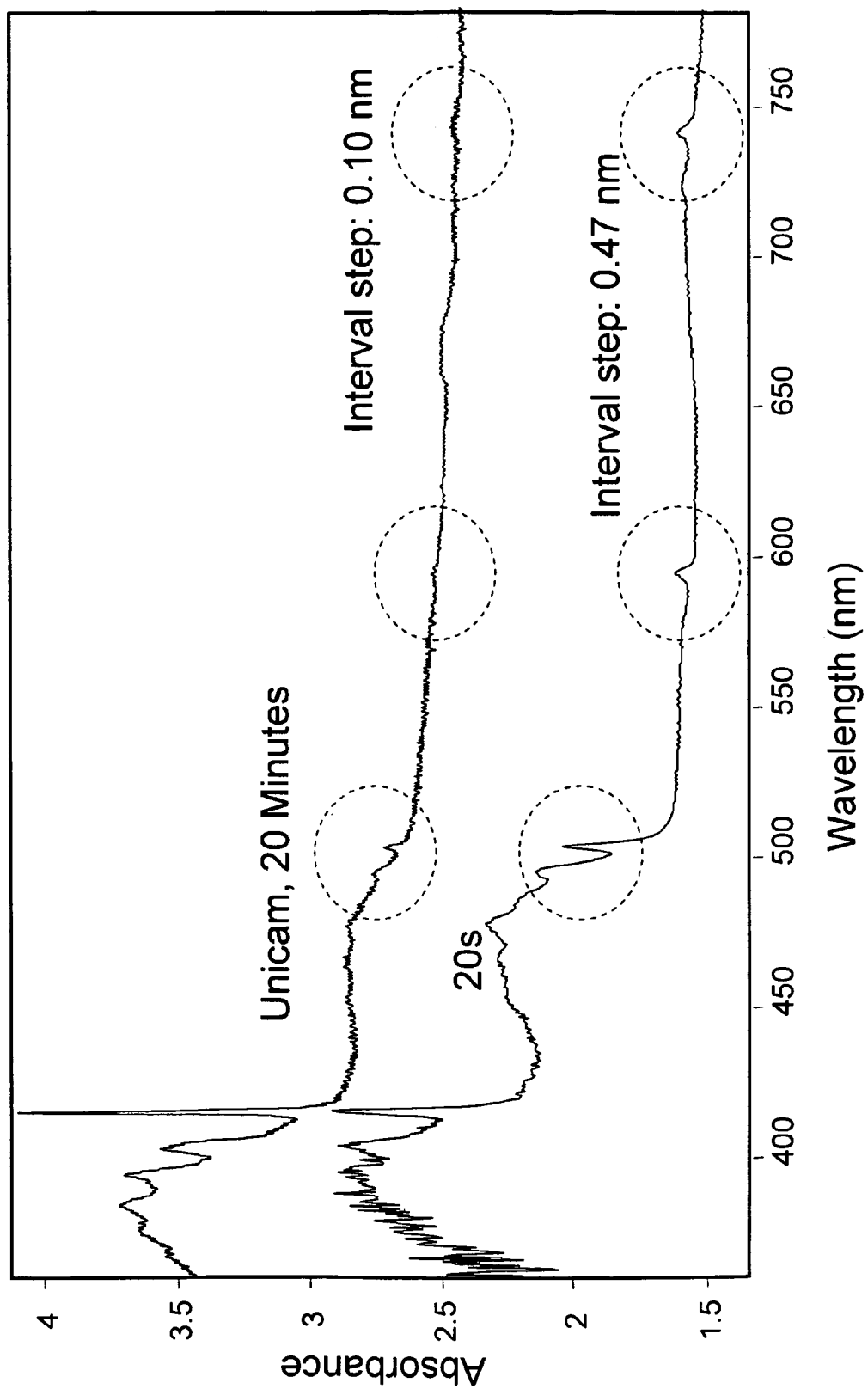
FIG. 3F is an exemplary graph comparing the spectral analysis of a 2.5 carat gem obtained using an apparatus of the prior art versus an apparatus according to an embodiment of the invention.

In FIG. 3F, an exemplary graph comparing the spectral response of a 2.5 carat gem obtained using an apparatus of the prior art versus an apparatus according to an embodiment of the invention is provided. For this particular graph, the spectrum (plotted at an interval step of 0.47 nanometers) for the gem collected by the present invention for twenty seconds, is compared to a spectrum (plotted at an interval step of 0.10 nanometers) of the same gem cooled by a prior art apparatus, which required a cooling time of approximately twenty minutes and data acquisition of another twenty minutes. As illustrated, not only are the plots relatively similar for the wavelength region below 450 nanometers, but the quality of the spectrum for wavelengths greater than 450 nanometers obtained using the present invention is markedly cleaner and higher sensitivity than the spectrum obtained using the prior art apparatus. Namely, through the use of the present invention a spectrum was obtained with much less noise, much more defined peaks, and substantially more quickly than that obtained using the prior art arrangement (see e.g., the peaks at approximately 503, 595, and 741 nanometers).

Figure 4:
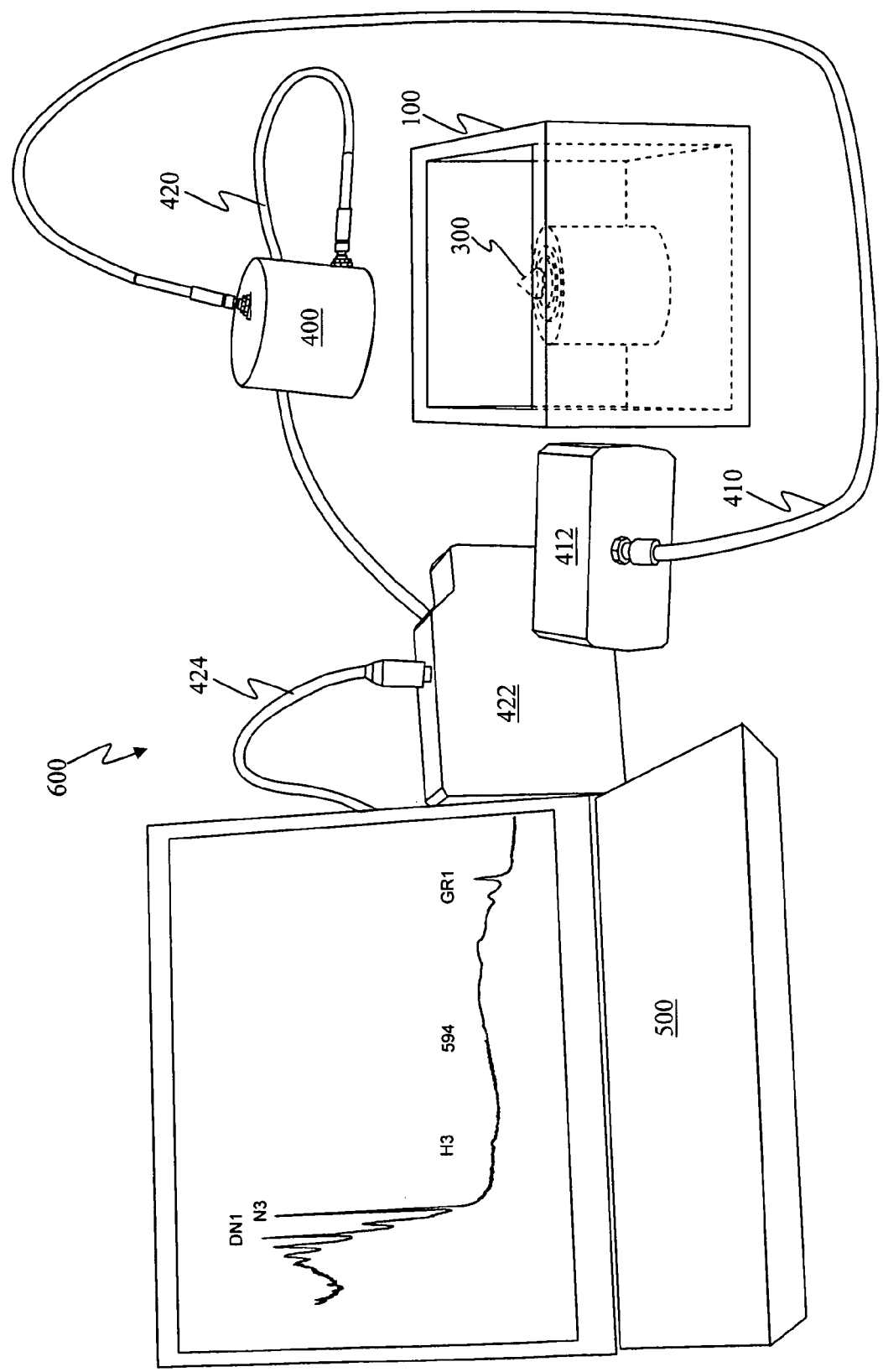
FIG. 4 is a schematic of a system employing an embodiment of a cooling apparatus according to an embodiment of the invention.

Referring to FIG. 4, the components of an embodiment of a gem spectral analysis system 600 which incorporates the cooling structure of the present invention will now be briefly described. Such a gem spectral analysis system may be that which is described in the "Gem Spectral Analysis System Application" referenced hereinabove.

In gem spectral analysis system 600, gem cooling apparatus 100 is provided for cooling an object 300 being evaluated to a desired temperature. An integrating sphere unit 400 is placed over an object 300. Object 300 is cooled to the desired temperature by cooling apparatus 100. Although reference is made to gem cooling apparatus 100, it is to be understood that the embodiments of gem cooling apparatus 102 and 104 may also be used in gem spectral analysis system 600.

Integrating sphere unit 400 illuminates the object 300 with electromagnetic radiation, which may be light of selected wavelengths, and then gathers the spectral response of the illuminated gem. Integrating sphere unit 400 may be implemented using model no. AvaSphere-50, manufactured by Avantes BV of Eerbeek, Netherlands. The selected wavelengths of light for illuminating object 300 may be provided by a light source 412, such as a tungsten halogen light source model AVALight-Hal-S, manufactured by Avantes BV of RB Eerbeek, Netherlands. Optical cable 410 may be used to route light from light source 412 to the integrating sphere unit 400. The gathered spectral response from integrating sphere unit 400 may be routed over optical cable 420 to a high resolution spectrometer unit 422, such as model no. HR4000, manufactured by Ocean Optics of Dunedin, Fla. The high resolution spectrometer unit 422 measures the amount of light as a function of wavelength in the gathered spectral response and transforms the measurements into digital information. The gathered spectral response data, in digital form, is then provided for further processing by computer 500. Cable 424 may be used to couple spectrometer unit 422 to computer 500 to provide a path for the spectral response data.

Computer 500 preferably includes software applications by which the spectral response information from spectrometer unit 422 may be further processed. Such processing may be for purposes of displaying an image on a computer screen of a depiction of the spectral response as a function of wavelength, as shown in FIG. 4, for detecting and analyzing characteristics of the spectral response, for extracting specified data from the spectral response information, and the like. Although a laptop computer is depicted in FIG. 4, it is to be understood that other computing or processing devices such as a desktop computer or dedicated controller unit, and the like, may be used, with or without an image display, within the spirit of the present invention.

The present invention has been described above with reference to several different embodiments. However, those skilled in the art will recognize that changes and modifications may be made in the above described embodiments without departing from the scope and spirit of the invention. Furthermore, while the present invention has been described in connection with a specific processing flow, those skilled in the art will recognize that a large amount of variation in configuring the processing tasks and in sequencing the processing tasks may be directed to accomplishing substantially the same functions as are described herein. These and other changes and modifications which are obvious to those skilled in the art in view of what has been described herein are intended to be included within the scope of the present invention.

What is claimed is:

1. A cooling apparatus comprising:
   a container having walls, except at one end, wherein the container is configured to contain a coolant within a space enclosed by the walls, wherein the interior of the container has a single planar bottom;
   a cooling block positioned substantially within the space on the bottom of the container and being surrounded by a continuous space, wherein the cooling block is configured such that when a sample is placed thereon at least a portion of the sample is above the cooling block, wherein the cooling block has a high heat capacity, and wherein the space surrounding the cooling block is filled with a coolant to a level at or below a top face of the cooling block; and
   a placement structure positioned on top of the cooling block and outside of the coolant-filled space, wherein the placement structure is in direct contact with the sample, has a high thermal conductivity and is attached to the top of the cooling block through a mechanism which promotes thermal conduction between the placement structure and the cooling block, wherein the coolant cools the cooling block which cools the placement structure which in turn cools the sample, and further wherein the container walls have a height and the cooling block has a height, and the height of the container walls are substantially the same as the height of the cooling block.

2. The cooling apparatus of claim 1, wherein a perimeter formed by the walls is circular.

3. The cooling apparatus of claim 1, wherein the placement structure comprises TEFLON® or SPECTRALON®.

4. The cooling apparatus of claim 1, wherein the cooling block has a bottom surface, a top surface and one or more side walls, wherein each of the one or more side walls of the cooling block is surrounded by the continuous space, and wherein the bottom surface of the cooling block is on the planar bottom of the container.

5. A cooling apparatus comprising:
a container having an open end defined by a perimeter, wherein the interior of the container has a single planar bottom;
a cooling block positioned within the container on the bottom of the container and being surrounded by a continuous space, wherein the cooling block is configured such that when a sample is placed thereon at least a portion of the sample is above the cooling block, wherein the cooling block has a high heat capacity, and wherein the space between the cooling block and walls of the cooling apparatus is filled with a coolant to a level at or below a top face of the cooling block, wherein the coolant cools the cooling block which cools the placement structure which in turn cools the sample, and further wherein the perimeter has a height and the cooling block has a height, and the height of the perimeter is substantially the same as the height of the cooling block; and
a placement structure positioned outside of the coolant-filled space and in fixed contact with the top face of the cooling block that is accessible at the open end of the container, wherein the placement structure is in direct contact with the sample and has a high thermal conductivity.

6. The cooling apparatus of claim 5, wherein the placement structure is configured to engage with an integrating sphere.

7. The cooling apparatus of claim 5, wherein the perimeter is square.

8. The cooling apparatus of claim 5, wherein the cooling block has a bottom surface, a top surface and one or more side walls, wherein each of the one or more side walls of the cooling block is surrounded by the continuous space, and wherein the bottom surface of the cooling block is on the planar bottom of the container.

9. A cooling apparatus comprising:
a container configured to contain a coolant within a space and to have an open end wherein the interior of the container has a single planar bottom;
a cooling block positioned substantially within the space on the bottom of the container and being surrounded by a continuous space, wherein the cooling block is configured such that when a sample is placed thereon at least a portion of the sample is above the cooling block, wherein the cooling block has a high heat capacity, and wherein the space surrounding the cooling block is filled with a coolant to a level at or below a top face of the cooling block, wherein the coolant cools the cooling block which cools the placement structure which in turn cools the sample, and further wherein the container has a height and the cooling block has a height, and the height of the container is substantially the same as the height of the cooling block; and
a placement structure friction-fit to the cooling block and external to the space filled with the coolant, wherein the placement structure is in direct contact with the sample has a high thermal conductivity.

10. The cooling apparatus of claim 9, wherein the container is shaped to accommodate an optical path line of an integrating sphere.

11. The cooling apparatus of claim 9, wherein the placement structure is configured to engage with an integrating sphere.

12. The cooling apparatus of claim 9, wherein the cooling block has a bottom surface, a top surface and one or more side walls, wherein each of the one or more side walls of the cooling block is surrounded by the continuous space, and wherein the bottom surface of the cooling block is on the planar bottom of the container.

13. A method for cooling an object comprising:
inserting a coolant into a container configured to contain the coolant within a coolant-space and to have an end which remains open, wherein the interior of the container has a single planar bottom; and
placing the object directly on a placement structure outside the coolant-space, wherein the placement structure has a high thermal conductivity, is coupled to a cooling block, and is cooled separately from the object, and wherein the cooling block has a high heat capacity and is positioned substantially within the coolant-space on the bottom of the container and being surrounded by a continuous space around the one or more side walls, wherein the coolant cools the cooling block which cools the placement structure which in turn cools the object, wherein the cooling block is configured such that when the object is placed thereon at least a portion of the object is above the cooling block, and further wherein the container has a height substantially the same as a height of the cooling block, and the coolant is inserted to a height lower than a height of the placement structure.

14. The method of claim 13 further comprising engaging an integrating sphere with the placement structure.

15. The method of claim 13, wherein the cooling block has a bottom surface, a top surface and one or more side walls, wherein each of the one or more side walls of the cooling block is surrounded by the continuous space, and wherein the bottom surface of the cooling block is on the planar bottom of the container.

16. A method for cooling an object comprising:
pouring a coolant into a space bounded by a container having an end which is open to air, wherein the interior of the container has a single planar bottom; and
positioning the object directly on a placement structure having a high thermal conductivity, wherein, before the object is positioned on the placement structure, the placement structure is coupled to a cooling block having a high heat capacity and positioned substantially within the space with the bottom surface on the bottom of the container and being surrounded by a continuous space around the one or more side walls, and wherein the object is positioned apart from the space occupied by the coolant, wherein the coolant cools the cooling block which cools the placement structure which in turn cools the object, wherein the cooling block is configured such that when the object is placed thereon at least a portion of the object is above the cooling block, and further wherein the container has a height substantially the same as a height of the cooling block, and further comprising pouring the coolant to a height lower than a height of the placement structure.

17. The method of claim 16 further comprising engaging an integrating sphere with the placement structure.

18. The method of claim 16, wherein the cooling block has a bottom surface, a top surface and one or more side walls, wherein each of the one or more side walls of the cooling block is surrounded by the continuous space, and wherein the bottom surface of the cooling block is on the planar bottom of the container.

19. A cooling apparatus comprising:
a container having walls, wherein the container is configured to contain a coolant within a space enclosed by the walls and to be open at one end, wherein the interior of the container has a single planar bottom;
a cooling block having a bottom surface, a top surface and one or more side walls, positioned substantially within the space with the bottom surface on the bottom of the container and being surrounded by a continuous space around the one or more side wall, wherein the cooling block has a high heat capacity and is configured such that when a sample is placed thereon at least a portion of the sample is above the cooling block, and wherein a portion of the space not occupied by the cooling block is filled with a coolant to a level at or below a top face of the cooling block, wherein the coolant cools the cooling block which cools the placement structure which in turn cools the sample, and further wherein the container walls have a height substantially the same as a height of the cooling block; and
a placement structure positioned on top of and affixed to the cooling block and outside of the coolant-filled space, wherein the placement structure is in direct contact with the sample has a high thermal conductivity and comprises aluminum.

20. The cooling apparatus of claim 19, wherein the cooling block has a bottom surface, a top surface and one or more side walls, wherein each of the one or more side walls of the cooling block is surrounded by the continuous space, and wherein the bottom surface of the cooling block is on the planar bottom of the container.

21. A method for cooling an object comprising:
inserting a coolant into a container having an open end and configured to contain the coolant within a coolant-space, wherein the interior of the container has a single planar bottom;
pre-cooling the object to a coolant temperature, and
placing the pre-cooled object directly on a placement structure outside the coolant-space, wherein the placement structure has a high thermal conductivity and comprises aluminum and is coupled to a cooling block, wherein the cooling block has a bottom surface, a top surface and one or more side walls, and wherein the cooling block has a high heat capacity and is positioned substantially within the coolant-space with the bottom surface on the bottom of the container and being surrounded by a continuous space around the one or more side walls, wherein the cooling block is configured such that when the object is placed thereon at least a portion of the object is above the cooling block, and the coolant is inserted to a height lower than a height of the placement structure, wherein the coolant cools the cooling block which cools the placement structure which in turn cools the object, and further wherein the container has a height substantially the same as a height of the cooling block.

22. The method of claim 21, wherein the cooling block has a bottom surface, a top surface and one or more side walls, wherein each of the one or more side walls of the cooling block is surrounded by the continuous space, and wherein the bottom surface of the cooling block is on the planar bottom of the container.

* * * * *